United States Patent
Armstrong et al.

(10) Patent No.: US 9,112,474 B2
(45) Date of Patent: *Aug. 18, 2015

(54) FLUID BASED RC FILTER FOR TUNING CUT-OFF FREQUENCY AND FOR ANALYTICAL DETECTION

(75) Inventors: Daniel W. Armstrong, Arlington, TX (US); Yasith S. Nanayakkara, Arlington, TX (US); Hyejin Moon, Fort Worth, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 513 days.

This patent is subject to a terminal disclaimer.

(21) Appl. No.: 13/213,675

(22) Filed: Aug. 19, 2011

(65) Prior Publication Data
US 2013/0138359 A1     May 30, 2013

Related U.S. Application Data

(60) Provisional application No. 61/375,066, filed on Aug. 19, 2010.

(51) Int. Cl.
   *G06F 17/00*    (2006.01)
   *H03H 5/00*    (2006.01)
   *G01N 27/02*    (2006.01)

(52) U.S. Cl.
CPC ............... *H03H 5/003* (2013.01); *G01N 27/02* (2013.01); *G01N 27/028* (2013.01); *G06F 17/00* (2013.01)

(58) Field of Classification Search
USPC ............. 702/23, 22, 19; 73/54.14, 54.02
See application file for complete search history.

(56) References Cited

PUBLICATIONS

Nanayakkara et al. (A tunable ionic liquid based RC filter using electrowetting: A new concept; vol. 2—No. 7, Jun. 29, 2010).*
Nanayakkara et al. "A Fundamental Study on Electrowetting by Traditional and Multifunctional Ionic Liquids: Possible Use in Electrowetting on Dielectric-Based Microfluidic Applications", Analytical Chemistry, vol. 80, No. 20 (2008).
Jiraseree-Asmornkun et al. "Theoretical Analysis of Highly Linear Tunable Filters Using Switched-Resistor Techniques", IEEE Reg. Papers, vol. 55, No. 11 (2008).
Nanayakkara et al. "The Effect of AC Frequency on the Electrowetting Behavior of Ionic Liquids", Analytical Chemistry, vol. 82, No. 8 (2010).
Zeng et al. "Principles of droplet electrohydrodynamics for lab-on-a-chip", Lab Chip, 2004, 4.
Cordella, Christophe "Principal component analysis: the basic building block of chemometrics", Actualite Chimique, vol. 345 (2010).
Wijethunga et al. "On-Chip Drop-to-Drop Liquid Microextraction Coupled with Real-Time Concentration Monitoring Technique", Anal. Chemical, vol. 83 (2011).
Jones, Thomas B. "On the Relationship of Dielectrophoresis and Electrowetting", Langmuier vol. 18 (2002).

(Continued)

*Primary Examiner* — John Breene
*Assistant Examiner* — Hien Vo
(74) *Attorney, Agent, or Firm* — Stephen J. Terrell; Parks Wood, LLC

(57) ABSTRACT

An RC filter that is tunable in terms of its cut-off frequency comprising a drop placed on one or more dielectric layers, a conducting layer underneath the dielectric layer, a nonconducting layer underneath the conducting layer, and an external resistor attached to the drop via an electrode, wherein the cut-off frequency of the filter is tuned by changing the shape or composition of the drop and methods of using the filter as a detector.

20 Claims, 8 Drawing Sheets

(56) References Cited

PUBLICATIONS

Nanayakkara et al. "High Throughput Chemical Analysis", University of Texas at Arlington, Abstract No. 200-2 (2010).
Moon et al. "Low voltage electrowetting-on-dielectric", AIP Journal of Applied Physics, 92, 4080 (2002).
Raj et al. "Ion and Liquid Dependent Dielectric Failure in Electrowetting Systems", Langmuier vol. 25 (2009).
Han et al. "High-Precision Digital-to-Analog Tunable Capacitors With Improved Quality Factor Using a Parallel Digital Actuator Array", Journal of Microelectromechanical Systems, vol. 18, No. 4 (2009).
Jones et al., "Frequency-Dependent Electromechanics of Aqueous Liquids: Elctrowetting and Dielectrophoresis", Langmuier, vol. 20 (2004).
Kumar et al. "Finite conductivity effects and apparent contact angle saturation in AC electrowetting", Mater. Res. Soc. Symp. Proc. vol. 899E (2006).
Shapiro et al. "Equilibrium behavior of sessile drops under surface tension, applied external fields, and material variations", AIP Journal of Applied Physics, vol. 93 (2003).
Mugele et al. "Electrowetting: from basics to applications", Journal of Physics Condens. Matter 17 (2005).
Millefiorini et al. "Electrowetting of Ionic Liquids", J. Am. Chem. Soc., vol. 128 (2006).
Chatterjee et al. "Electromechanical model for actuating liquids in a two-late droplet microfluidic device", Lab Chip, vol. 9 (2009).
Widegren et al. "Electrolytic conductivity of four imidazolium-based room-temperature ionic liquids and the effect of a water impurity", J. Chem Thermodynamics, vol. 37 (2005).
David J. Anderson "Determination of the Lower Limit of Detection", Clinical Chemistry, vol. 35, No. 10 (1989).
Lazzari et al. "Capacitance response of carbons in solvent-free ionic liquid electrolytes", Electrochemistry Communications, vol. 9 (2007).
Schreiner et al. "Fractional Walden Rule for Ionic Liquids: Examples from Recent Measurements and a Critique of the So-Called Ideal KCl Line for the Walden Plot", J. Chem. Eng. Data, vol. 55 (2010).
EWG's Skin Deep Cosmetic Database: Info for Cetrimonium Chloride.
EWG's Skin Deep Cosmetics Database: Info for Benzalkonium Chloride.
Ren et al. "Automated on-chip droplet dispensing with volume control by electro-wetting actuation and capacitance metering", Sensors and Actuators B, vol. 98 (2004).
Terol et al. "Simple and rapid analytical method for the simultaneous determination of cetrimonium chloride and alkyl alcohols in hair conditioners", International Journal of Cosmetic Science, vol. 32 (2010).
Prince et al. "Analysis of benzalkonium chloride and its homologs: HPLC versus HPCE", Journal of Pharmaceutical and Biomedical Analysis, vol. 19 (1999).
Gong et al. "All-electronic droplet generation on-chip with real-time feedback control for EWOD digital microfluidics", Lab Chip vol. 8 (2008).
Agilent Impedance Measurement Handbook—A guide to measurement technology and techniques, 4th Edition (2009).
Shin et al. "A CMOS Active-RC Low-Pass Filter With Simultaneously Tunable High- and Low-Cutoff Frequencies for IEEE 802.22 Applications", IEEE Transactions on Circuits and Systems-II: Express Briefs, vol. 57 (2010).
Swart et al. "A Voltage-Controlled Tunable Distributed RC Filter", IEEE Journal of Solid-State Circuits, Aug. (1972).
Nanayakkara et al. "A Tunable Ionic Liquid Based RC Filter Using Electrowetting: A New Concept", ACS Applied Materials & Interfaces, vol. 2, No. 7 (2010).
Nanayakkara et al. "A liquid drop RC filter apparatus for detection", Anal. Bioanal Chem, vol. 401 (2011).
Shin et al. "A feedback control system for high-fidelity digital microfluidics" Lab Chip, vol. 11 (2011).

* cited by examiner

FLUID BASED RC FILTER FOR TUNING CUT-OFF FREQUENCY AND FOR ANALYTICAL DETECTION

CROSS REFERENCE TO RELATED APPLICATION

This application claims priority to U.S. Provisional Application Ser. No. 61/375,066 filed on Aug. 19, 2010, the contents of which are hereby incorporated by reference.

BACKGROUND OF THE INVENTION

The field of the invention is RC filters. More specifically the invention is related to an RC filter employing a fluid drop to form one of the capacitors. The gain vs. frequency curve of the RC filter is changeable by changing the fluid drop shape or composition. The RC filter can be used as a tunable RC filter, where the cut-off frequency can be tuned or as an analytical detector.

A resistor-capacitor (RC) circuit is an electronic circuit composed of resistors and capacitors. RC circuits can be used as RC filters when they are used to filter a signal by attenuating unwanted frequency elements of a specific signal. The gain vs. frequency curve of a RC filter typically is a function of the R (resistor) and C (capacitor) values.

A solid-fluid interface can act as a capacitor in the presence of an external electric field. If a fluid drop is placed on a dielectric surface such as Teflon, then that system can be modeled as a resistor-capacitor network and thus act as an RC filter. In such a system, the dielectric layer and the solid-fluid interface act as serially connected capacitors plus the fluid drop acts as a resistor connected in parallel to the latter capacitor. Adding an extra traditional resistor to this system results in a fluid drop based RC filter.

Electrowetting is the reduction of contact angle (making a surface more wettable by a liquid) by an applied voltage. Electrowetting on dielectric (EWOD) is when a thin dielectric layer is inserted between the electrode and the liquid to emulate the electric double layer in conventional electrowetting. The ideal dielectric blocks electron transfer, while sustaining the high electric field at the interface that results in charge redistribution when a potential is applied. When a hydrophobic dielectric is used, the large initial contact angle provides room for a large contact angle change upon electrowetting. Furthermore, by employing a dielectric layer between the liquid and electrode, virtually any kind of liquid can be used, regardless of the polarization of the interface.

Electrowetting on dielectric (EWOD) is now being accepted as one of the major ways for manipulating droplets in micro total analysis systems (µTAS) or lab-on-a-chip devices, where surface tension is one of the dominant forces. The advantages of a lab-on-a-chip device with electrowetting include negligible Joule heating, no moving micromechanical parts, and accurate and quick manipulation of droplets by digitally addressing of electrodes.

It would be useful to have an RC filter for which the cut-off frequency can be shifted within a tuning range and that can be tuned to a certain value according to the needs to achieve a particular purpose.

It would be useful to have a fluid drop based RC filter that can be used as a detector to detect an analyte in the fluid drop.

SUMMARY OF THE INVENTION

The invention provides an RC filter that is tunable in terms of its cut-off frequency and that can be used to detect analytes. The cut-off frequency can be shifted within a tuning range and can be tuned to a certain value according to the needs to achieve a particular purpose.

The RC filter includes a liquid or gas drop on a dielectric surface. The dielectric layer and the solid-fluid interface of the drop behave as serially connected capacitors and the drop acts as a resistor connected in parallel to the latter capacitor. An external resistor is connected to the drop via an electrode. The filter further includes a conducting layer under the dielectric layer and can include a nonconducting layer under the conducting layer.

The total value of the capacitance of the filter is a function of the solid-fluid interface capacitance and the dielectric layer capacitance. With other components being constant, the total capacitance of the filter is a function of the conductivity, surface tension, and dielectric constant of the drop. Therefore the total capacitance is different from liquid to liquid or gas to gas. In particular, the capacitance will change when a substance is extracted into the drop. The change in the capacitance of the drop will thus change the gain vs. frequency curve of the filter. Therefore, the gain vs. frequency curve of the filter can be used to identify and quantify most substances in or on the drop, such as heavy metals, biocides, biological molecules, and other analytes.

The total capacitance is a function of the area between the drop and the dielectric layer, and this area is dependent on the shape of the drop or the contact angle. The shape (or the contact angle) of the drop can be controlled by electrowetting; therefore the total capacitance can be tuned by electrowetting.

At a given frequency, the gain of the RC filter is ultimately a function of the conductivity ($\sigma$), dielectric constant ($\in$), surface tension ($\gamma$), and double layer thickness (d) of the drop and the applied voltage ($V_{in}$) [i.e., gain=$F(\sigma,\in,\gamma,d,V_{in})$]. For a given fluid, $\sigma$, $\in$, $\gamma$, and d values are constant; therefore gain only depends on $V_{in}$. One can change the gain vs. frequency curve by changing $V_{in}$, hence the cut-off frequency can be changed accordingly (the frequency at which gain equals to −3 dB is called cut-off frequency). Drops of different fluids have different $\sigma$, $\in$, $\gamma$, and d values, which means the gain vs. frequency curve generated by a certain fluid at constant $V_{in}$ is unique. For a solution prepared by dissolving an analyte in a pure fluid, the $\sigma$, $\in$, $\gamma$, and d values are different from those values of the pure fluid, and accordingly so is the generated gain vs. frequency curve. Depending on the properties of the analyte and the concentration of the analyte, the change of gain vs. frequency curve can vary. Therefore the relationship between $\sigma$, $\in$, $\gamma$, and d values and the gain vs. frequency curve can be used to detect the analyte. The use of the RC filter as a detector is based on this relationship.

The filter can be used as a standalone detector or can be coupled with a droplet based microfluidic lab-on-a-chip system such as an EWOD based microfluidic chip.

The detector has a number of advantages over existing detection techniques and devices including the need for a very small sample volume and low sample consumption. Therefore the detector is ideal for expensive or low volume samples. The detector can be fabricated and operated with very low cost. The device can be designed to be used as a standalone device to determine or to validate concentration, pH, and purity of electrolytes, buffers, and other solutions. Thus it may be useful in many ways for an ordinary laboratory. The detector can also be used as a portable device. The signal source can easily be generated by a computer program such as Labview and can be supplied through a USB port.

Another advantage is that the device can easily be integrated with EWOD based lab-on-a-chip systems such as EWOD based liquid-liquid extraction devices. Since most EWOD based systems operate on AC voltages the same signal source can be used to operate the detector.

DETAILED DESCRIPTION OF THE INVENTION

Figure 1A:
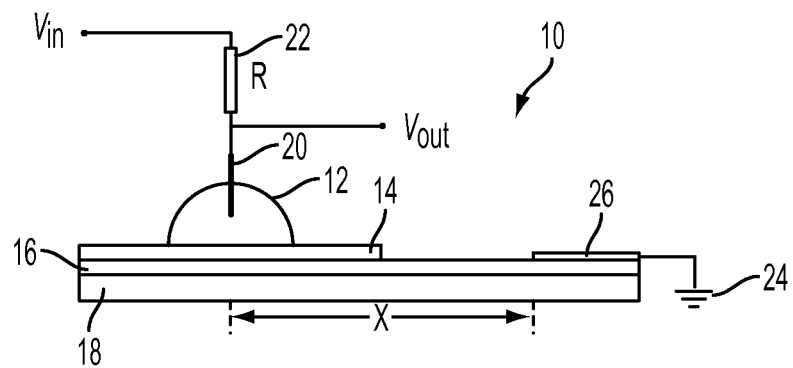
FIG. 1a is a schematic illustration of a filter in accordance with the invention.
Figure 1B:
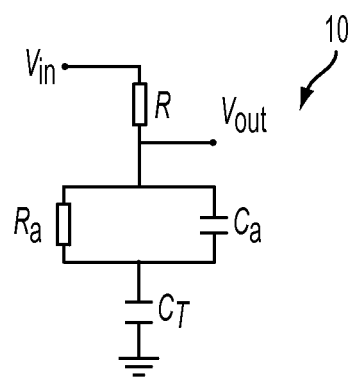
FIG. 1b is a schematic illustration of the electrical circuit of the filter.

The basic theory of the RC filter is discussed above. FIGS. 1a and 1b illustrate such a system 10. As shown in FIG. 1a, a liquid drop 12 is placed on a dielectric layer 14. Below the dielectric layer are a conducting layer 16 and a glass slide 18. An electrode 20 is dipped into the liquid drop 12 and an external resistor 22 is attached to the drop via the electrode. A ground electrode 24 is connected to the conducting layer 16 via an aluminum contact pad 26. V$_{in}$ is applied voltage and V$_{out}$ is voltage out. Referring to FIG. 1b, R$_a$ is the resistor value of the liquid drop 12 and C$_a$ is the capacitance value of the solid-liquid interface. C$_T$ is the capacitance value of the dielectric layer 14. R is the resistor value of the external resistor 22.

Fundamental calculations show that for this kind of system, at a given frequency, the gain is a function of R$_a$, C$_a$, and C$_T$ as represented in equation (1):

$$\text{gain} = F(R_a, C_a, C_T) \quad (1)$$

However, R$_a$ is a function of the conductivity ($\sigma$) of the liquid drop and the contact angle ($\theta$) of the liquid drop. Therefore at constant V$_{in}$ the liquid drop resistance is expressed by equation (2):

$$R_a = F(\sigma, \theta) \quad (2)$$

Also, C$_a$ is a function of the dielectric constant ($\in$), double layer thickness (d), and the contact angle ($\theta$) of the liquid drop. Therefore at constant V$_{in}$ the C$_a$ is expressed by equation (3):

$$C_a = F(\in, d, \theta) \quad (3)$$

In addition, C$_T$ is a function of the contact angle (O). Therefore at constant V$_{in}$, $$C_T = F(\theta) \quad (4)$$

According to the Young-Lippman equation, at constant V$_{in}$, contact angle ($\theta$) is a function of surface tension ($\gamma$) and dielectric constant ($\in$):

$$\theta = F(\gamma, \in) \quad (5)$$

Therefore by combining equations 1, 2, 3, 4 and 5, at constant V$_{in}$, and at given frequency, gain can be written as equation (6):

$$\text{gain} = F(Y, \in, d, \gamma) \quad (6)$$

According to equation 6, gain is a function of $\sigma$, $\in$, d, and $\gamma$ (conductivity of the liquid drop, dielectric constant, double layer thickness of the liquid drop, and surface tension of the liquid drop), and the applied voltage V$_{in}$.

Traditionally, a plot of frequency versus gain has been used to characterize RC filters. By convention, the frequency at which gain equals −3 dB is called the cut-off frequency (f$_C$) or critical frequency of the RC filter. Although in electronics −3 dB was chosen by convention as the f$_C$, it is an arbitrary choice. Hence the concentration of solutions may not always be directly correlated with f$_C$ values. However, when a frequency versus gain curve is transformed into different axes using Principle Component Analysis (PCA), a clear unique peak can be observed. The relationship between a frequency versus gain curve and the PCA curve is described by equations 7 and 8, where PC1 is Principal Component Axis 1, PC2 is Principal Component Axis 2, f is frequency, g$_f$ is gain of RC filter for a given frequency, and N is the number of data points.

$$PC1 = \frac{0.7071}{s_f} f + \frac{-0.7071}{s_g} g_f \quad (7)$$

$$PC2 = \frac{-0.7071}{s_f} f + \frac{-0.7071}{s_g} g_f \quad (8)$$

where, $$s_f = \sqrt{\frac{1}{N} \sum_{i=1}^{N} (f - \bar{f})^2} \,;$$

$$s_f = \sqrt{\frac{1}{N} \sum_{i=1}^{N} (g - \bar{g})^2}$$

Using computer software such as C$^{++}$ or Labview, one can acquire a final transformed curve in microseconds for a given analyte. These types of mathematical transformations are common in analytical instruments. Fourier transformation is a well-known example of such a mathematical transformation.

Drops of different liquids have different $\sigma$, $\in$, $\gamma$, and d values, which means the gain vs. frequency curve generated by a certain liquid drop is unique. Consider a solution prepared by dissolving an analyte in a pure liquid. The $\sigma$, $\in$, $\gamma$, and d values of the analyte solution are different from those of the pure liquid, and accordingly the generated gain vs. frequency curve for the analyte solution also is different from that of the pure liquid. The change of the gain vs. frequency curve can vary depending on the properties and concentration of the analyte. This variance can easily be visualized when gain vs. frequency curves are transformed into different axes using Principal Component Analysis (PCA), a well-known statistical technique for data analysis and processing. The relationship between σ, ∈, γ, d values and the transformed gain vs. frequency curve can easily be used to detect the analyte. Consequently a detector can be developed based on that relationship.

The liquid RC filter of the invention relies on tuning the cut-off frequency by changing the $V_{in}$ and keeping other factors constant or the transformed gain vs. frequency curve (peak) when one of the variables σ, ∈, γ, or d changes and keeping the $V_{in}$ constant.

The detector can be used to detect charged and/or dielectrically different species dissolved in a fluid (e.g., water, alcohol, mixtures, gas).

Filter Design

Figure 2:
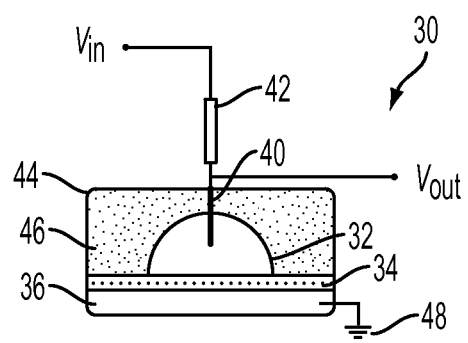
FIG. 2 is a schematic illustration of a second embodiment of a filter in accordance with the invention.
Figure 3:
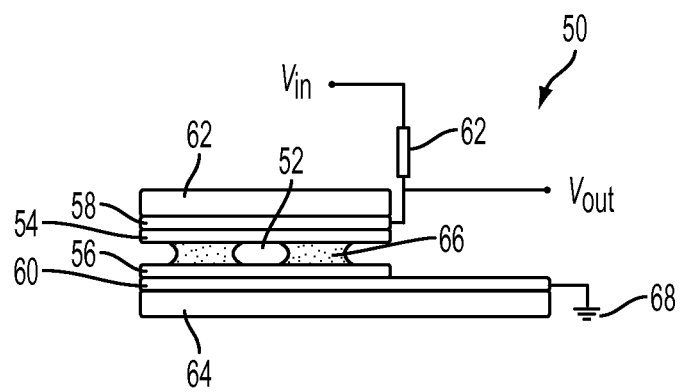
FIG. 3 is a schematic illustration of a third embodiment of a filter in accordance with the invention.

The general structure of a filter is discussed above and shown in FIG. 1. FIGS. 2 and 3 illustrate alternative embodiments of the filter. In FIG. 2, the filter 30 includes the drop 32, dielectric layer 34, and conducting layer 36. An electrode 40 is dipped into the drop 32 and an external resistor 42 is attached to the drop via the electrode 40. In this embodiment, the drop 32, dielectric layer 34, conducting layer 36, and electrode 40 are encased within a plastic compartment 44. A media 46 such as organic solvent, silicone oil, or air is also encased within the compartment 44. FIG. 2 is especially relevant for volatile substances. The drop 32 can be liquid or gas, volatile or nonvolatile, and the media 46 serves to hold the drop is place. A ground electrode 48 is connected to the conducting layer 36.

FIG. 3 illustrates filter 50 as a microfluidic or digital microfluidic device for analyzing a sample in liquid or gas form. Filter 50 includes the drop 52 and two parallel dielectric layers, top dielectric layer 54 and bottom dielectric layer 56. Two conducting layers 58 (top) and 60 (bottom) sandwich the dielectric layers 54, 56 and drop 52. Two glass slides 62 (top) and 64 (bottom) then sandwich the conducting layers 58, 60. Bottom conducting layer 60 and bottom glass slide 64 extend further than dielectric layers 54, 56 and top conducting layer 58, and top glass slide 62, all of which are substantially the same length. An external resistor 62 is attached to the drop via the conducting layer 58 which serves as the electrode. A media 66 such as organic solvent, silicone oil, or air is entrapped between the top and bottom dielectric layers 54, 56. A ground electrode 68 is connected to the bottom conducting layer 60.

Alternatively the device shown in FIG. 3 can be used to detect analytes in fluid flows (for example as a detector in liquid chromatography). In such instances a fluid drop is not necessary, either a flowing fluid or stationary fluid channel or fluid patch can be used. In such a device a hollow dielectric tube can be used instead of parallel dielectric plates.

Filter Components

The Fluid

The fluid contains the analyte to be assayed. The drop size can range from about 100 picoliters to 50 microliters. The drop size will vary depending on the device design and the analyte. In addition, the Ca, $C_T$ and Ra values (and thus total capacitance) of the filter can be changed by changing the drop size. A microfluidic device will typically use a smaller drop size, such as about 100 pL to 1 μL. A gas drop will typically be in the range of about 1 to 100 μL.

The sample amount needed for a proof of principle detector was 5 μL. In previous reported EWOD experiments very low sample volumes (about 100 pL) were used. Other recent work used about 200 nL size droplets to demonstrate liquid-liquid extraction on an EWOD based lab-on-chip device.

The analyte can theoretically be any ion or molecule of any molecular weight. The concentration of the analyte can range from about 1 part per billion (ppb) to 100%.

Dielectric Layers

The dielectric layers are composed of one or more layers of one or more dielectric materials such as the fluoropolymers Teflon® and Cytop® (an amorphous fluoropolymer), silicon dioxide ($SiO_2$), or any other dielectric material. A preferred material is Teflon®, since it shows good reversibility and ease of use. However, Teflon layers usually have small pin holes in them, and electrons can penetrate through these holes creating a leakage current, which can reduce the performance of the filter. Coating another dense dielectric material like $SiO_2$ beneath the Teflon layer can minimize the leakage current. The voltage which is required to achieve a certain Δθ can be reduced by reducing the thickness of the dielectric layer. However, most thin dielectrics exhibit numerous failure modes. Hence one should decrease the dielectric thickness with analysis of reliability for better operation. If the reliable thinner dielectric is achievable, then that may allow the use of even lower voltage to tune the $f_C$ values. Preferably the dielectric layer ranges from about 50 angstroms to 25 microns in width.

Conducting Layers

The conducting layers are preferably made of indium tin oxide (ITO) but can alternatively be of another conducting material such as gold, silver, or copper. Preferably they have a thickness between about 10 angstroms and 1 mm.

Electrode

The electrode can be platinum, stainless steel, or any other material from which electrodes are generally made.

Glass Slide

The glass slide is optional as its purpose is simply to provide support for the device. Preferably the glass slide is clear to ensure optical transparency required for fluorescence based assays. The glass slide can be glass, plastic, silicon, or any other nonconducting material.

Resistor

The resistance value can be changed to change the performance and range of the fc. Preferably the resistor has a value of from about 1 picoohm to 1000 megaohms.

Applied Voltage

An increase in applied voltage means the contact angle (θ) of the fluid drop will decrease. As a consequence, the contact area of the drop on the Teflon surface will increase, thus increasing the total capacitance of the system. An increase in capacitance will result in a decrease in the $f_C$ value. Generally the applied voltage will range from 1 nano volt to 1000 volts.

Ionic Liquid

Room Temperature Ionic liquids (RTILs) are popular due to their unique properties such as negligible vapor pressure, higher thermal stability, and physiochemical properties that can be tuned depending on the application. One useful ionic liquid is 1-butyl-3-methylimidazolium bis-Orifluoromethyl-sulfonyl)imide, abbreviated [bmim][$NTf_2$]. Use of [bmim][$NTf_2$] has several practical advantages including: (i) evaporation is not a concern since it has negligible or no vapor pressure and no special sealing or packaging is needed for the filter; (ii) it has resistance to vibrations and satellite drop formation, particularly compared to water or aqueous electrolytes; (iii) it has a lower viscosity than most ILs so that response times are faster than other ILs; (iv) the apparent contact angle change ($\Delta\theta$) of [bmim][NTf$_2$] due to frequency (not voltage) is lower than that of other ILs; (v) ion adsorption to the Teflon® surface is minimal, since it contains a bulky NTf2 anion; and (vi) it has a negligible effect of water when compare to other ILs.

However, other ILs can be used and may be advantageous since different ILs have different capacitance due to their structure and the nature of their functional groups. Also, the $\Delta\theta$ is different for different ILs, i.e., some ILs exhibit higher $\Delta\theta$ at a given voltage, whereas other ILs show lower $\Delta\theta$ at the same voltage. Therefore, if one needs a wide tunability range of $f_C$, it is desirable to use the first type of ILs, and for fine-tunability the latter types of ILs are desirable.

Other Variables

The lower limit of detection (LOD) and the performance of the detector can be improved by altering or controlling any of several factors. Peaks can be shifted either to a lower or higher frequency range by changing any of several elements of the filter. Lower frequency ranges are better to identify more conductive analytes whereas higher frequency ranges are better to identify more dielectric analytes.

The $C_a$, $R_a$, and $C_T$ values can be changed by changing the drop size. The $C_T$ value also can be tuned by changing the dielectric layer material. In the Examples herein, Teflon® was used as the dielectric material because of its versatility. However, thin Teflon® layers are usually imperfect and can be susceptible to leakage current across the dielectric layer which ultimately reduces the performance of the detector. Another dielectric material such as SiO$_2$ can be used to minimize the leakage current.

In the Examples ITO pre-coated commercial glass slides were used due to their low cost. However, due to high resistivity of the ITO coating (about 100 Ω/cm) the ITO layer can act as an extra resistor in the system. Also, the resistance caused by ITO can have different values depending on the position of the analyte drop. That can affect the gain vs. frequency curve. Therefore, the analyte drop was always positioned at a constant length away from the aluminum contact pad for every experiment (3 cm away for detection and 5 cm away for tuning). This effect can be reduced using gold, silver, or any other highly conducting material coated glass slides. However that can elevate the fabrication cost of the device, since gold coated glass slides are approximately 20 times more expensive than ITO coated glass slides. Also at higher frequencies impedance generated from the connecting wires can affect the gain vs. frequency curve. This effect can be minimized by using minimum amounts of connecting wires.

Applications

The filter can be used in any application where it would be useful to have an RC filter whose cut-off frequency can be tuned. As described above, the cut-off frequency can be tuned by changing the characteristics of the liquid or gas drop. Characteristics include the composition of the drop (the liquid or gas and any added components) as well as the size and dimensions of the drop. As discussed above, the dimensions of the drop can be changed by electrowetting.

As a detector, the filter has a variety of industrial and biomedical applications including analysis of colon and blood electrolyte levels, drug levels, glucose levels, analysis of bulk chemicals, and environmental analyses. Applications for the filters include devices for detection of biocides, metal ions, gases, and concentration determination of electrolytes, acids, and bases. The filters could be used with any fluid including biological fluids such as urine, saliva, cerebrospinal fluid, or any gas etc. As one example, a filter could be used to identify people with renal failure by analyzing the dissolved ammonia levels in saliva. This detector can be developed into a USB plug and play device and potentially mass manufactured for under $100, although more elaborate and expensive devices may be desirable as well.

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. In the examples, unless expressly stated otherwise, amounts and percentages are by weight, temperature is in degrees Celsius or is at ambient temperature, and pressure is at or near atmospheric.

Experimental Details

Unpolished float glass slides coated with 30 nm thick indium-tin-oxide (ITO) were purchased from Delta Technologies Ltd., (Stillwater, Minn.). The slides were dip coated with Teflon solution prepared with 4% (w/v) of Teflon AF1600 (www2.dupont.com) in Fluoroinert FC75 solvent (www.fishersci.com). A custom made device was used to perform dipcoating, where the approximate dipping speed was set to 0.78±0.03 mm/s. Once 75% of the slide was dipped in the solution, dipping was stopped for 5 seconds, and then the slide was raised at the same speed. The coated slides were allowed to condition in an oven for 6 min at 112 C, 5 min at 165 C and 15 min at 328 C. Once Teflon coated glass slides reached room temperature, they were washed thoroughly with acetone and deionized water and air-dried. A Tencor Alphastep 200 Profilometer was used to measure the thickness of the coated Teflon layer, which was 260±10 nm.

A drop of analyte (5.0±0.5 μL) was placed on top of the Teflon layer using a micropipette. A 32 gauge Pt wire was inserted into the analyte drop so that the distance between the Pt tip and Teflon surface was exactly 0.8 mm. The other end of the Pt wire was connected to a 82 kΩ resistor. The input signal was fed through this resistor. The ITO layer is used as the ground electrode of the system. An aluminum contact pad was used to make the connection between the ITO layer and the system. The analyte drop was always kept constant distance apart from the Al contact pad to minimize the error caused by the ITO resistance (3 cm apart for detection and 5 cm apart for tuning). A sinusoidal signal generated by a waveform generator (Agilent Model 33220A) connected to a voltage amplifier (Trek Model PZD 350) was used as the input signal. The amplitude of the signal was kept at 50 VRMS at all times. The frequency of the signal was increased logarithmically from 200 Hz to 140 kHz with a 50 s sweep time. Input and output data were collected from a PC based oscilloscope (www.picotech.com). First gain vs. frequency curves were plotted for DI water. Then principal component analysis (PCA) was used to obtain equations 7 and 8 [Matlab software (www.mathworks.com) was used to perform PCA]. After that, equations 7 and 8 were used to transform gain vs. frequency curves for all analytes. $f_C$ values were extracted from gain vs. frequency plots. The experiments were monitored with a contact angle goniometer (CAM 101, www.ksvltd.com).

Anhydrous ZnCl$_2$ was purchased from Sigma-Aldrich (St. Louis, Mo.). Benzalkonium chloride (BAC) reference standard was purchased as 10% (w/v) aqueous solution from the United States Pharmacopeia (store.usp.org). As per the catalog, the homolog distribution of the reference standard was 0.1% C10, 68% C12, 25% C14 and 5% C16 and <0.1% C18 in weight percentages. Cetyltriethyl-ammonium chloride (CTAC) was purchased from Sigma-Aldrich (St. Louis, Mo.). 1-methylimidazole was purchased from Sigma-Aldrich (St. Louis, Mo.). All aqueous solutions were prepared with DI water (resistivity-18 MΩ·cm) and all experiments were performed in room temperature (22±1° C.) unless otherwise noted.

Example 1

Tuning the Cut-Off Frequency Via Electrowetting

Figure 4:
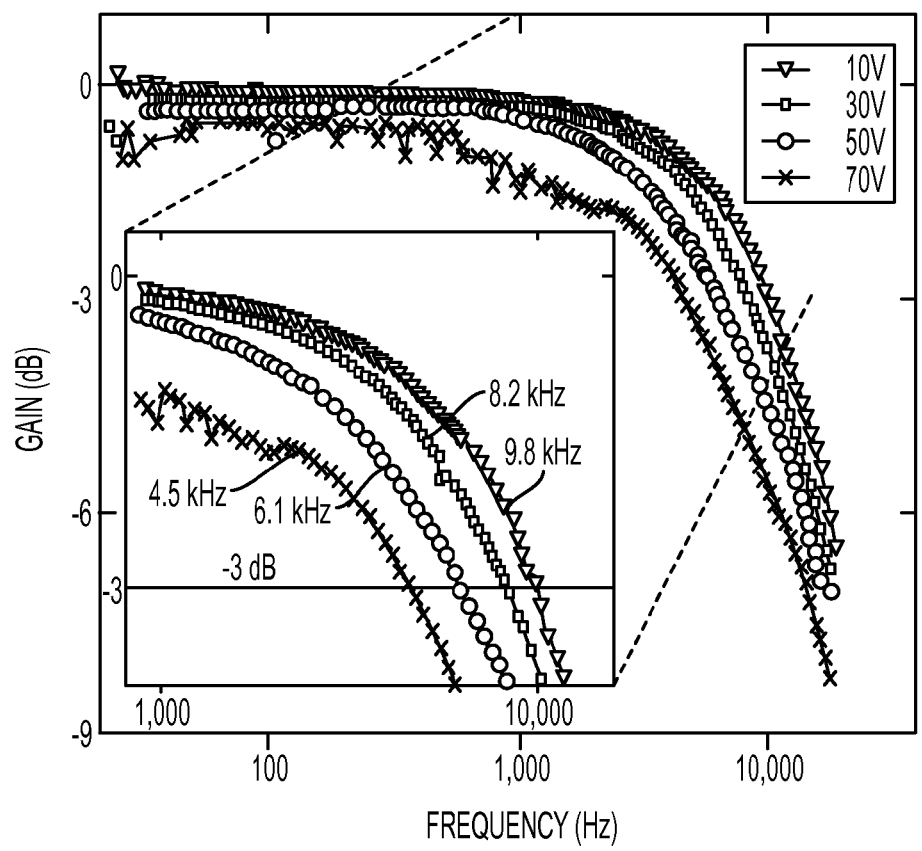
FIG. 4 illustrates frequency vs. gain plots of [bmim][NTf$_2$] ionic liquid at different V$_{in}$.

The ionic liquid (IL) 1-butyl-3-methylimidazolium bis(trifluoromethylsulphonyl)imide, abbreviated [bmim][NTf$_2$] was synthesized in our laboratory as reported previously. Before use, the IL was kept in a vacuum oven for 18 hours with phosphorous pentoxide (P$_2$O$_5$) at room temperature to minimize the water content. The final water content of the IL, measured by Karl Fischer titration was 470 ppm. Then a 5 μl drop of IL was tested with the RC filter as shown in FIG. 1. FIG. 4 shows the frequency versus gain plot of the IL based RC filter. It can be observed from the plot that at 10 V$_{rms}$ the obtained f$_c$ is 9.8 kHz, whereas at 30V, 50 V, and 70 V the obtained f$_c$'s are 8.2 kHz, 6.1 kHz, and 4.5 kHz respectively.

Example 2

Detection of Heavy Metals

RTILs can be molecular engineered to extract heavy metals selectively. The RTIL 1-butyl-3-methylimidazolium bis(trifluoromethylsulphonyl)imide ([bmim][NTf$_2$]), which can be used to extract heavy metals such as Pb, Au, and Fe, was used for this example. The metals were extracted into the RTIL from wastewater. Then 5 microliter drops of the RTIL with extracted metal were tested with the RC filter as shown in FIG. 1. The cut-off frequencies of the RTILs with extracted metal were different than that of pure RTIL. Qualitative analysis can be carried out by changing the type of RTIL. This qualitative information can be gleaned since each analyte/solute will have a unique gain vs. frequency curve when detected under identical conditions. Indeed sweeping frequency at different voltages could provide a characteristic profile of a compound in a manner somewhat analogous to that of a diode array detector providing distinct UV spectra. The results indicated that this could be a versatile method to analyze heavy metals in wastewater.

A gain vs. frequency plot was used to determine the f$_C$ of the heavy metal analytes. First, a 10 V sinusoidal signal was supplied to the system, increasing the frequency from 20 Hz to 18.5 kHz logarithmically with a 140 s sweep time. This procedure was repeated for 30 V$_{rms}$, 50 V$_{rms}$ and 70 V$_{rms}$ sinusoidal signals.

Table 1 shows the calculations of cut-off frequency for these liquids. Since the cut-off frequencies are different for the different analytes, this method can be used to detect the particular analytes.

TABLE 1

| | Cut-off frequency (f$_C$) values at different voltages | | | |
|---|---|---|---|---|
| | f$_C$ at 10 V | f$_C$ at 30 V | f$_C$ at 50 V | f$_C$ at 70 V |
| Pure IL | 9.8 kHz | 8.2 kHz | 6.1 kHz | 4.5 kHz |
| IL with Pb | 6.7 kHz | 5.2 kHz | 3.7 kHz | 2.2 kHz |
| IL with Au | 8.2 kHz | 7.0 kHz | 5.8 kHz | 4.6 kHz |
| IL with Fe | 5.6 kHz | 4.3 kHz | 3.0 kHz | 1.8 kHz |

Example 3

Cetyltriethyl-Ammonium Chloride (CTAC) Detection

CTAC, also known as cetrimonium chloride or hexadecyl trimethyl ammonium chloride, is an antiseptic, antistatic agent, and fabric softener, typically used in shampoos and hair conditioners. CTAC is used as an active agent in over 1000 commercial products. Due to its lack of a chromophore, uv-vis detectors are not effective in detection of CTAC, but conductimetric, refractive index (RI), evaporative light scattering (ELS) and mass spectrometry (MS) based detection methods are used. Each of these detection methods has its advantages and disadvantages: for example, RI and ELS are low sensitive methods whereas MS is a very expensive method.

Figure 5A:
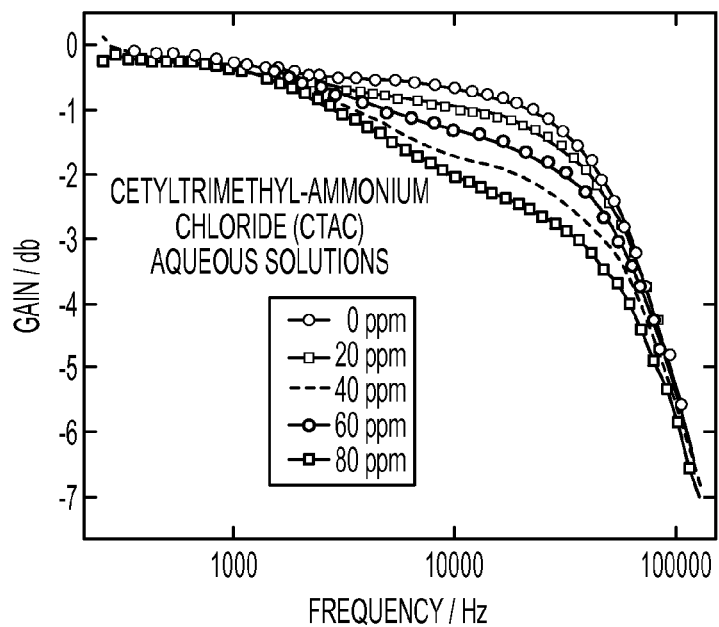
FIG. 5a shows gain vs. frequency curves of cetyltriethylammonium chloride (CTAC) aqueous solutions.
Figure 5B:
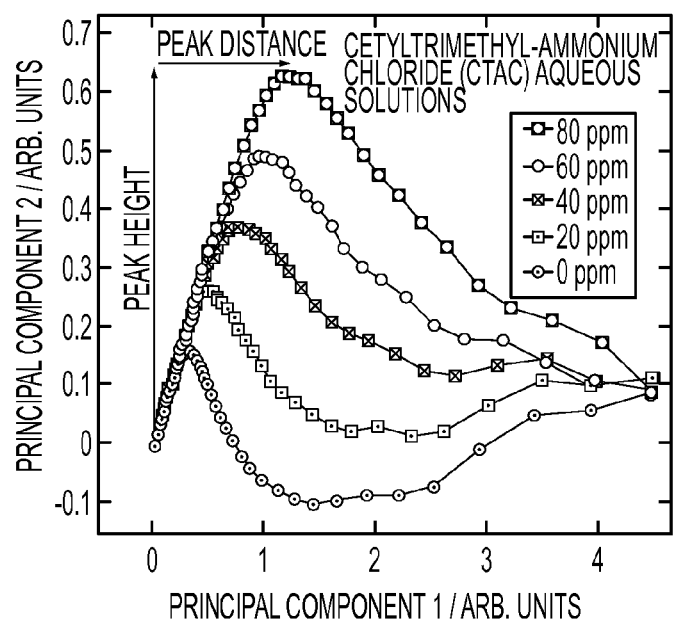
FIG. 5b illustrates the gain vs. frequency curves transformed into different axes using principal component analysis for better visualization and characterization.
Figure 6:
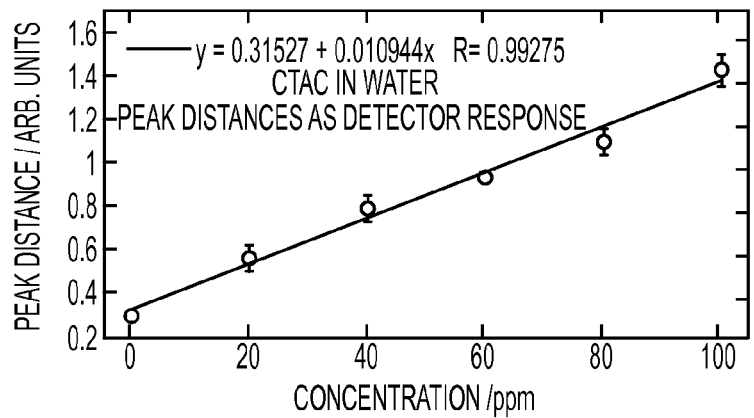
FIG. 6 is a calibration plot of CTAC solutions concentration vs. peak distance.
Figure 7:
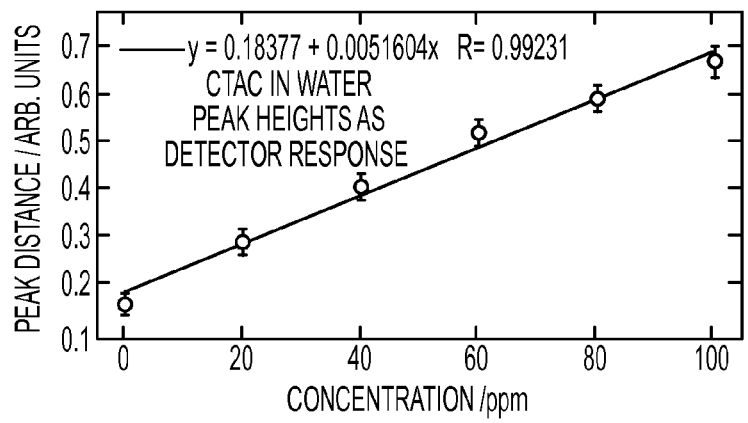
FIG. 7 is a calibration plot of CTAC solutions concentration vs. peak height.

Standard aqueous solutions of CTAC were prepared and tested with the detector. Each test utilized a 5 μL sample volume. FIG. 5a shows the gain vs. frequency curves of the CTAC aqueous solutions and FIG. 5b illustrates the gain vs. frequency curves transformed into different axes using principal component analysis for better visualization and characterization. FIG. 6 is a calibration plot of the CTAC solutions Peak Distances as detector response and FIG. 7 is a calibration plot of CTAC solutions Peak Heights as detector response. It can be observed that each solution has a characteristic peak and the concentration of the solution is proportional to the both peak height and peak distance. This provides two different ways to obtain standard curves. Clearly both peak distances and peak heights provide very good linear relationships (R=0.99 for both) with the concentrations of CTAC.

Figure 8:
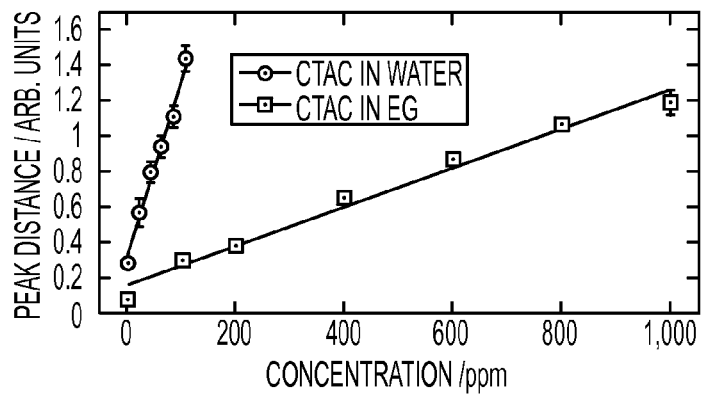
FIG. 8 illustrates concentration vs. peak distance for CTAC solutions in water and in ethylene glycol.

To study the effect of solvent, different concentrations of CTAC in ethylene glycol (EG) also were tested. FIG. 8 shows the calibration plots of peak distance versus concentration obtained for CTAC solutions prepared with DI water and EG. Clearly solvent plays a role although both solutions gave linear graphs. This may be due to the conductivity differences of CTAC in the two solvents. Since EG is much more viscous than water, the conductivity of CTAC/EG is much lower than that of CTAC/water (Walden's rule).

Example 4

Zinc Chloride (ZnCl$_2$) Detection

Standard aqueous solutions of ZnCl$_2$ were prepared and tested with the detector using 5 μL sample volumes. Each sample was tested at least 4 times using 3 different glass slides.

Figure 9A:
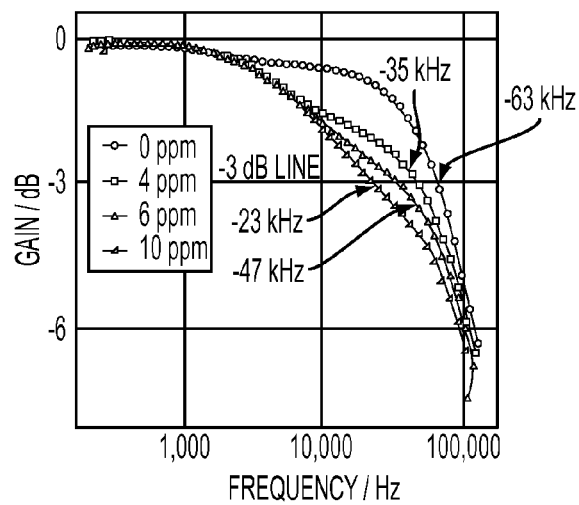
FIG. 9a is a frequency vs. gain plot for selected ZnCl$_2$ solutions.
Figure 9B:
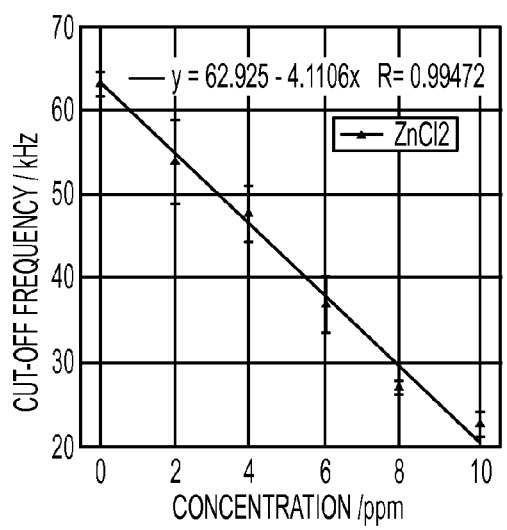
FIG. 9b is a chart of concentration vs. cut-off frequency for selected ZnCl$_2$ solutions.
Figure 9C:
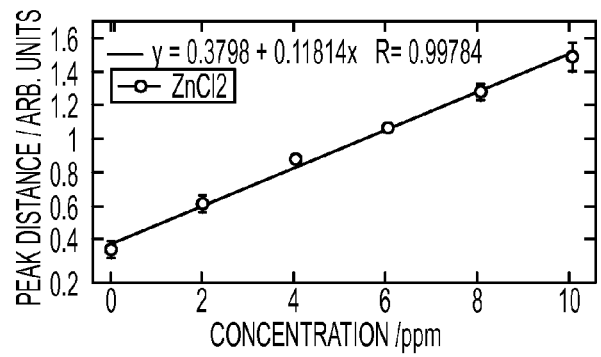
FIG. 9c is a plot of concentration versus peak distance for selected ZnCl$_2$ solutions.

FIG. 9a shows the frequency versus gain plots for the ZnCl$_2$ solutions. The intersection point of the gain curves and the −3 dB line gives the f$_C$ value. Each solution has a different f$_C$ value and the concentration of the solution is inversely proportional to the f$_C$ value (note that the frequency axis in FIG. 9a is logarithmic in scale). FIG. 9b shows the relationship between f$_C$ and the concentration of ZnCl$_2$, when the f$_C$ values extracted from FIG. 9a were plotted against concentration values of the ZnCl$_2$ solutions. Clearly f$_C$ has a very good linear relationship (R=0.995) with the concentrations of ZnCl$_2$ solutions. FIG. 9c shows the relationship between concentration and peak distance (R=0.99784). These charts can thus be used as calibration curves.

Example 5

Detection of Benzalkoniuin Chloride (BAC)

The RC filter was used to detect the industrially important biocide benzalkonium chloride (BAC). BAC is a mixture of alkylbenzyldimethylammonium chlorides with even-numbered alkyl chain lengths which range from n-C8H17 to n-C18H37. BAC is a popular biocide which is used as a preservative in over 155 commercial cosmetic, disinfectant and ophthalmic products. Each homolog of BAC has different bactericidal activities; therefore the United States Pharmacopeia-National Formulary (USP-NF) regulates the percentage of each homolog of BAC.

Standard aqueous solutions of BAC were prepared and tested with the detector using 5 µL sample volumes. Each sample was tested at least 4 times using 3 different glass slides.

Figure 10A:
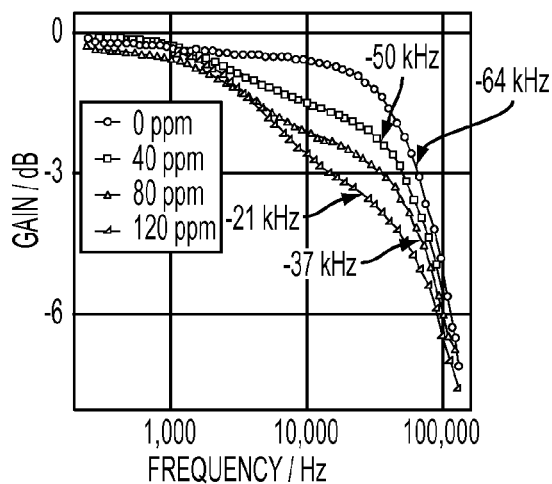
FIG. 10a is a frequency vs. gain plot for selected BAC solutions.
Figure 10B:
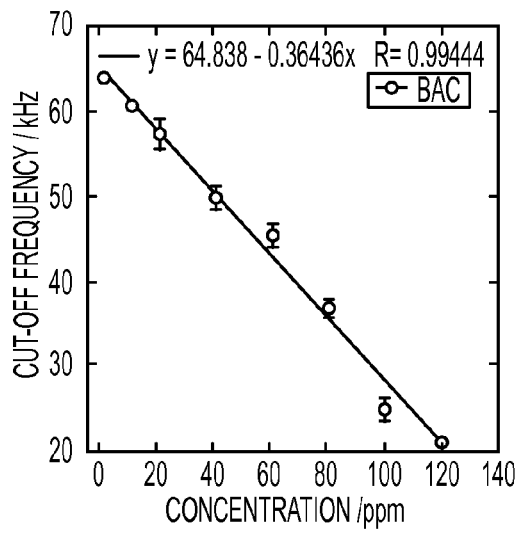
FIG. 10b is a chart of BAC concentration vs. cut-off frequency for selected BAC solutions.
Figure 10C:
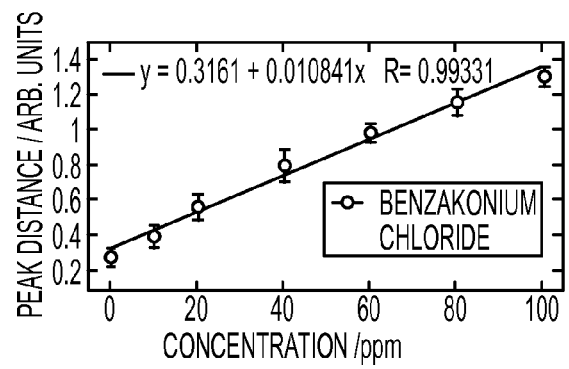
FIG. 10c is a plot of concentration versus peak distance for selected BAC solutions.

FIG. 10a shows the frequency versus gain plots for selected BAC solutions. FIG. 10b illustrates that a linear relationship (R=0.994) was obtained for concentration vs. cut-off frequency. FIG. 10c shows that a linear relationship is also present for concentration vs. peak distance.

Example 6

1-Methylimidazole Detection

Figure 11:
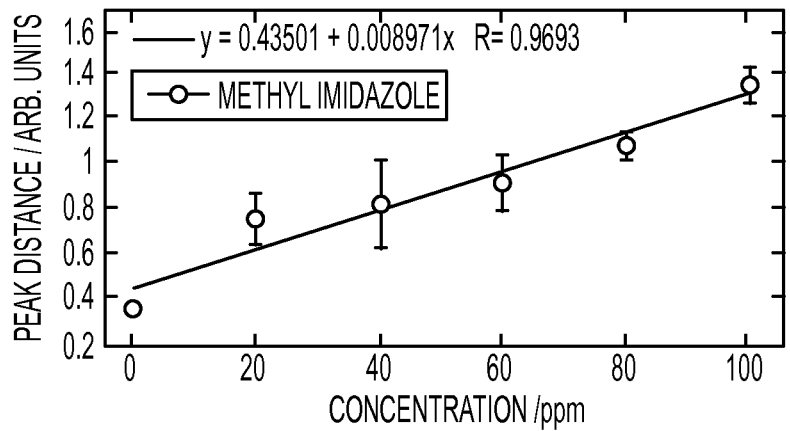
FIG. 11 is a chart of concentration vs. peak distance for 1-methylimidazole solutions.

Aqueous solutions of 1-methylimidazole were prepared and tested with the detector. Each test utilized a 5 µL sample volume. FIG. 11 shows the calibration plot for the 1-methylimidazole aqueous solutions, where a linear relationship (R=0.954) between peak distance and concentration was obtained. 1-methylimidazole aqueous solutions are non-ionic and this result indicates that not only ionic compounds, but also non-ionic compounds can be detected using this device.

Example 7

Droplet Shape

Figure 12:
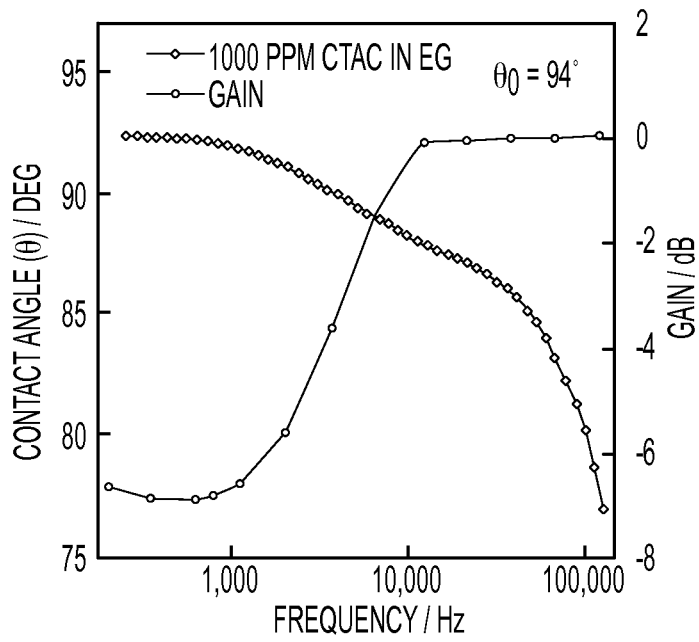
FIG. 12 is a chart of frequency vs. contact angle and gain for CTAC in ethylene glycol solutions.

It was observed that during the frequency sweep an analyte drop adjusts itself to different shapes. To investigate that phenomenon, the contact angle of a 1000 ppm CTAC/EG drop was recorded for selected frequencies. FIG. 12 shows these results. Initially when there is no voltage/frequency applied to the drop, the 1000 ppm CTAC/EG has a $\theta$ of 94° (which is called Young's angle or the contact angle at zero external voltage $-\theta_0$). When 50 V/200 Hz voltage is applied to the drop, $\theta$ decreases from 94° to 78°. Keeping the voltage constant, if frequency is increased, $\theta$ decreases. However after a threshold it starts to increase until it achieves a constant value. The phenomenon further supports the existence of the RC filter type effect in this experiment, which can be easily visualized by the corresponding gain vs. frequency plot.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. An RC filter, comprising:
a first dielectric layer;
a fluid drop in contact with the first dielectric layer;
a first conducting layer, wherein the first dielectric layer is between the fluid drop and the first conducting layer;
a conducting element in contact with the fluid drop, the conducting element comprising one of:
an electrode; and
second layers including:
a second dielectric layer in contact with the fluid drop; and
a second conducting layer, wherein the second dielectric layer is between the second conducting layer and the fluid drop;
a resistor connected between a voltage input terminal and the conducting element; and
a voltage output terminal connected to a point between the resistor and the conducting element;
wherein a cut-off frequency of the filter is based on a shape and a composition of the fluid drop.

2. The RC filter of claim 1, wherein the shape of the fluid drop is based on a voltage applied by a voltage source between the voltage input and the first conducting layer.

3. The RC filter of claim 1, wherein the fluid drop includes a liquid or a gas.

4. The RC filter of claim 1, wherein the shape of the fluid drop includes a contact angle of the fluid drop to the first dielectric layer.

5. The RC filter of claim 1, wherein the composition of the fluid drop includes an analyte.

6. The RC filter of claim 1, wherein the first dielectric layer comprises a fluoropolymer.

7. The RC filter of claim 1, further comprising a media in contact with the fluid drop.

8. The RC filter of claim 7, wherein the media is selected from a group consisting of organic solvent, silicone oil, and air.

9. The RC filter of claim 1, wherein the fluid drop includes an ionic liquid.

10. A system, comprising:
an RC filter, comprising:
a first dielectric layer;
a fluid drop in contact with the first dielectric layer;
a first conducting layer, wherein the first dielectric layer is between the fluid drop and the first conducting layer;
a conducting element in contact with the fluid drop, the conducting element comprising one of:
an electrode; and
second layers including:
a second dielectric layer in contact with the fluid drop; and
a second conducting layer, wherein the second dielectric layer is between the second conducting layer and the fluid drop;
a resistor connected between a voltage input terminal and the conducting element; and
a voltage output terminal connected to a point between the resistor and the conducting element;
a voltage source configured to apply a voltage between the voltage input and the first conducting layer, wherein a cut-off frequency of the filter is based on a shape and a composition of the fluid drop; and
a voltage measurement device configured to measure a voltage between the voltage output terminal and the first conducting layer.

11. The system of claim 10, further comprising an analysis device, the analysis device comprising:
a memory comprising instructions that, when executed by a processor, cause the analysis device to perform operations comprising:

applying an input signal with the voltage source;
measuring an output signal with the voltage measurement device; and
generating a gain vs. frequency curve based on the input signal and the output signal.

12. The system of claim 11, the operations further comprising:
identifying a cutoff frequency of the gain vs. frequency curve; and
identifying an analyte based on comparing the cutoff frequency to a standard curve.

13. The system of claim 11, the operations further comprising:
generating a principal component curve, wherein values for each of a first principal component and a second principal component of the principal component curve are based on values of a frequency and a respective gain of the gain vs. frequency curve;
identifying a feature of the principal component curve, the feature selected from a group consisting of:
a peak height of the principal component curve; and
a peak distance of the principal component curve;
identifying a concentration of an analyte based on comparing the feature of the principal component curve to a standard curve.

14. The system of claim 10, further comprising an analysis device, the analysis device comprising:
a memory comprising instructions that, when executed by a processor, cause the analysis device to perform operations comprising:
applying a plurality of input signals with the voltage source, each of the plurality of input signals having a different voltage;
measuring a plurality of output signals with the voltage measurement device; and
generating a plurality of gain vs. frequency curves, each gain vs. frequency curve of the plurality of gain vs. frequency curves being based on one of the plurality of input signals and a respective one of the plurality of output signals;
identifying a plurality of cutoff frequencies, each cutoff frequency of the plurality of cutoff frequencies being identified in a respective one of the plurality of gain vs. frequency curves; and
identifying an analyte based on comparing the plurality of cutoff frequencies to a standard curve.

15. The system of claim 10, wherein the shape of the fluid drop is based on a voltage applied by the voltage source.

16. The system of claim 10, wherein the fluid drop includes a liquid or a gas.

17. The system of claim 10, wherein the shape of the fluid drop includes a contact angle of the fluid drop to the first dielectric layer.

18. The system of claim 10, wherein the first dielectric layer comprises a fluoropolymer.

19. The system of claim 10, further comprising a media in contact with the fluid drop.

20. A method, comprising:
applying an input signal to an RC filter with a voltage source;
measuring an output signal from the RC filter with a voltage measurement device;
generating a gain vs. frequency curve based on the input signal and the output signal; and
identifying an analyte or a concentration of an analyte based on the gain vs. frequency curve;
wherein the RC filter, comprises:
a first dielectric layer;
a fluid drop in contact with the first dielectric layer;
a first conducting layer, wherein the first dielectric layer is between the fluid drop and the first conducting layer;
a conducting element in contact with the fluid drop, the conducting element comprising one of:
an electrode; and
second layers including:
a second dielectric layer in contact with the fluid drop; and
a second conducting layer, wherein the second dielectric layer is between the second conducting layer and the fluid drop;
a resistor connected between a voltage input terminal and the conducting element; and
a voltage output terminal connected to a point between the resistor and the conducting element;
the voltage source, the voltage source being configured to apply a voltage between the voltage input and the first conducting layer, wherein a cut-off frequency of the RC filter is based on a shape and a composition of the fluid drop; and
the voltage measurement device, the voltage measurement device being configured to measure a voltage between the voltage output terminal and the first conducting layer.

* * * * *